(12) United States Patent
Buser

(10) Patent No.: US 6,217,897 B1
(45) Date of Patent: Apr. 17, 2001

(54) ORAL MUCOSAL COMPOSITION COMPRISING 5-AMINOSALICYLIC ACID

(75) Inventor: Thomas Buser, Ziefen (CH)

(73) Assignee: Tillotts Pharma AG, Ziefen (CH)

( * ) Notice: Subject to any disclaimer, the term of this patent is extended or adjusted under 35 U.S.C. 154(b) by 0 days.

(21) Appl. No.: 09/147,631

(22) PCT Filed: Aug. 12, 1997

(86) PCT No.: PCT/EP97/04376

§ 371 Date: Apr. 5, 1999

§ 102(e) Date: Apr. 5, 1999

(87) PCT Pub. No.: WO98/06387

PCT Pub. Date: Feb. 19, 1998

(30) Foreign Application Priority Data

Aug. 13, 1996 (GB) .................................... 9617001

(51) Int. Cl.$^7$ ...................................................... A61F 13/00
(52) U.S. Cl. ............................................ 424/434; 424/435
(58) Field of Search ...................................... 424/434, 435

(56) References Cited

FOREIGN PATENT DOCUMENTS

| | | |
|---|---|---|
| 0 352 826 * | 1/1990 | (EP) . |
| 352 826 | 1/1990 | (EP) . |
| 429 224 | 5/1991 | (EP) . |
| 9000237 * | 8/1991 | (NL) . |
| WO90/14076 | 11/1990 | (WO) . |
| WO95/26715 | 10/1995 | (WO) . |
| WO 95/26715 * | 10/1995 | (WO) . |

OTHER PUBLICATIONS

Ranzi et al. Successful treatment of genital and oral ulceration in Behcet's disease with topical 5–aminosalicylic acid (5–ASA) Br. J. Dermatology 120(3):471–472, 1989.*

Ranzi, T., et al., Br. J. Dermatology 120, No. 3, 471–472 (1989).

* cited by examiner

Primary Examiner—Thurman K. Page
Assistant Examiner—Todd D Ware

(57) ABSTRACT

A topical spreadable composition comprising 5-aminosalicylic acid (5-ASA) as active and monoolein is provided for treatment ulcers, inflammation and lesions of the oral cavity. The composition is spread over and adheres to the lesion, and is preferably prepared in a water free state. Examples of indications that can be treated are oral Crohn's Disease, apthous ulcers, orofacial granulomatosis, oral ulcers associated with Behet's disease and oral lichen planus.

9 Claims, No Drawings

ORAL MUCOSAL COMPOSITION COMPRISING 5-AMINOSALICYLIC ACID This invention relates to a 5-aminosalicylate acid (5-ASA) composition for the treatment or prophylaxis of oral ulcerations, inflammation and lesions of the oral cavity, and in particular the use the glyceryl monooleate in the preparation of such compositions.

Oral ulceration (or mouth ulcers) can be very painful and the resulting lesions can be mild or severe. There are various preparations for the treatment of oral ulcerations. For example carbenoxolone sodium can be helpful in promoting healing of mild oral lesions, lozenges and oral pastes containing corticosteroids are used for treating apthous non-specific ulcers, salicylates can be used in mild inflammatory and painful oral lesions, and benzydamine hydrochloride has a topical anti-inflammatory and analgesic effect and is used as a mouthwash or spray for oral ulcerations. A difficulty of treating oral ulcerations with preparations such as sprays, lozenges and mouthwash is that the active agent of the preparation is only transiently in contact with the ulcer. Even with gelatin based pastes, which have a protective effect for non-infected ulcers, it is difficult to keep them on the lesion for a prolonged period.

An example of a mucoprotectant is orabase™ which contains carmellose sodium, pectin and gelatin. This composition, however, has an uncomfortable gritty mouthfeel.

5-aminosalicylic acid (5-ASA) is a known compound and is currently used in the treatment of inflammatory bowel disease such as Crohn's disease and ulcerative colitis. For these indications, 5-ASA is administered rectally as an enema, or orally as a controlled release capsule. EP-A-0 352 826 relates to the use of 5-ASA for detmatological disorders associated with therapy-resistant loss of epithelium, such as pyoderma gangrenosum, leg ulcers, mouth ulcers, decubitus, bullous dermatoses and burns. In addition, 5-ASA is water sensitive and therefore it is desirable to formulate it in a substantially water free composition.

Topical 5-ASA in a guaze poultice has also been reported as treating oral and genital lesions resulting from Behcet's disease (British J. Dermatol., 1989, 120:471–72).

It is an object of the present invention to provide an effective treatment for oral ulceration, inflammation and lesions of the oral cavity, in particular of the tongue, gingivae, lips, palate and buccal mucosa.

We have now surprisingly found an effective medicament for treating oral ulcerations inflammation, and lesions of the oral cavity which comprises 5-ASA as active agent or a physiologically acceptable derivative thereof, and glyceryl monooleate. The glyceryl monooleate is conveniently spread in a thin film over the ulcer and forms an adhesive bond with the mucous of the ulcer, which in turn maintains the 5-ASA in contact with the ulcer for a prolonged period. Furthermore, we have found that the glyceryl monooleate can be used in a substantially water free state, which helps to stabilise the 5-ASA and prolong the shelf life of the composition.

Preferably, monoolein (containing glyceryl monooleate) is used in the composition of the invention.

By monoolein we mean a product which consists predominately of glyceryl monooleate, although various other glycerides of oleic acid and other fatty acids could be present. Hereinafter refernces to glyceryl monooleate should be construed also as a reference to monoolein (CAS Registry No. 25496-72-4) and visa versa.

Preferably glyceryl monooleate (and monoolein) is formulated in a substantially water-free state. This enhances the shelf life of the compositon.

Monoolein is a mixture of the glycerides of oleic acid and other fatty acids, consisting mainly of the glyceryl monooleate. A commercial form of monoolein is sold by Eastman Chemicals (e.g. at Hemel Hemstead, UK or Denver, USA) under the trade name Myverol™. The manufacturers recommended uses of Myverol™ are: for sustained release formulations, for topical permeation enhancement, for solubilisation of a water soluble drug into an oil matrix, and for sustained release microspheres. Monoolein is normally formulated in its fully hydrated cubic phase (which contains up to about 40% water) to produce its advantageous sustained release properties (J.Phy.Chem.1989, 93, 7304–7314 and EP-A-0 314 689).

A composition comprising monoolein and an active such as metronidazole (an antibacterial) is described in EP-A-0 671 175 and equivalent U.S. Pat. No. 5,261,164 as a sustained release product for treating periodontal disease. The composition is injected into the periodontal pocket, preferably by a syringe. Such a product is sold under the trade name elyzol™ which is issued with a disposable applicator for the treatment of chronic periodontal disease. Similar periodontal type applications of monoolein are disclosed in Pharmaceutical Technology Europe February 1995, p14–16, and J.Clin. Periodontal 1992; 19:687–692.

Accordingly in a first aspect of the present invention there is provided a spreadable mucoadhesive topical pharmaceutical composition comprising 5-ASA or a physiologically acceptable derivative thereof, and glyceryl monooleate.

By physiologically acceptable derivative, we mean a derivative which is metabolised in vivo, such as by the enzymes in the oral cavity, to the same active metabolite as 5-ASA, and in particular includes physiologically acceptable salts and esters of 5-ASA.

An example of a derivative of 5-ASA ia an N-acetyl derivative and its salts. Some esters have similar activity, e.g. alkyl esters, especially lower alkyl esters such as methyl, ethyl, propyl or isopropyl; alkenyl esters; cycloalkyl esters; aryl esters; alicyclic esters; and aralkyl esters.

Examples of physiologically acceptable salts of 5-ASA and its derivatives include salts derived from an appropriate base, such as an alkali metal (for example sodium or potassium), an alkaline earth metal (for example magnesium), ammonium or $NX4^+$, wherein X is a $C_{1-4}$ alkyl group.

Most oral ulcerations or lesions should respond to treatment with a composition of the present invention particularly including the following: oral aphthous ulcers, oral mucositis (including mucositis neuroticans agranulocytica), oral Crohn's disease, ulcers in patients with ulcerative colitis, orofacial granulomatosis, denture stromatitis, oral ulcers associated with Behet's Disease, oral lichen planus, pemphigus of the mouth, herpetic ulcers and traumatic lesions. By lesion we mean to include papule, nodule, weal, vesicle, bulla, plaque, scale, excoration, scar, and lichenification.

Oral mucositis is an inflammation of the oral mucous surface and, for example, can result from chemotherapy.

Symptoms of oral Crohn's disease can include thickening of the mucous membranes of the mouth and lip.

Symptoms of orofacial granulomatosis can include furrowing of the tongue, thickening of the lower lip and buccal mucosa, and recurrent aphthous ulcers.

The composition of the invention is ideally suited for treating oral ulceration, inflammation and lesions of the tongue, palate, lips, gingivae and most preferably the buccal mucosa.

Optional components which can also be used in the composition include anaesthetic agents, flavourings, surfactants, penetration enhancers, antioxidants, polymers, opacifiers, viscosity modifying agents including hydrocarbon waxes or oils such as glycerol. In a preferred embodiment white soft paraffin wax is used to improve the Theological behaviour of glyceryl monooleate (i.e. improve its spreadability). Surprisingly, the white soft paraffin also helps prevent sedimentation of solids in the formulation as compared to other oils such as paraffin, glycerol, and arachis oil.

Other preferred optional components are titanium dioxide as an opacifier, lidocaine hydrochloride as an anaesthetic, benzyl alcohol as a penetration enhancer and ascorbyl palmitate as an antioxidant. Ascorbyl palmitate is a particularly good antioxidant in a substantially water-free composition of the invention.

The amount of each component in a formulation can vary. Thus 5-ASA could be used at up to 20% w/w, more preferably 1% to 10% w/w, preferably 3% to 7% w/w and most preferably about 5% w/w. Glyceryl monooleate (or monoolein) can be present at 10% to 99% w/w, preferably 20% to 80% w/w, more preferably 40% to 60% w/w and most preferably about 50% w/w. Where the total weight is less than 100% w/w, the formulation would be made up with other optional components. For example, a hydrocarbon wax, such as white soft paraffin, is desirably used at 10% to 50% w/w, preferably 25% to 45% w/w, most preferably about 35% w/w. An anaesthetic agent, such as lidocaine, is desirably used at 1% to 5% w/w, preferably about 3% w/w. An antioxidant such as ascorbyl palmitate is desirably used at 0.1 to 1% w/w, preferably 0.3% to 0.7% w/w, most preferably about 0.5% w/w. Typically the composition can be administered in a 5 g or 10 g tube.

A particularly preferred embodiment of the invention includes 5-ASA or a physiologically acceptable salt thereof, at 3% to 7% w/w, glyceryl monooleate at 40% to 60% w/w, hydrocarbon wax, preferably white soft paraffin, at 25% to 45% w/w, anaesthetic, preferably lidocaine hydrochloride at 1% to 5% w/w, ascorbyl palpitate at 0.1% to 1% w/w, preferably 0.3 to 0.7% and optional other components.

The composition of the invention is typically supplied from a tube or pump dispenser and spread topically using the finger tip in a smearing action over, for example, the oral ulcer. In this way a thin mucoadhesive film is formed which is comfortable and convenient for the patient. In addition, the glyceryl monooleate film protects the ulcer from further infection and, because it is substantially insoluble in saliva, it prevents the 5-ASA from being washed off the ulcer. As such, with intermittent applications a therapeutically effective amount of 5-ASA can be maintained in continuous contact with the ulcerous lesion thereby accelerating healing of the lesion. Typically a 5 g tube of the composition will contain about one hundred doses.

Further aspects of the invention are as follows:
1. The use of glyceryl-monooleate as a mucoadhesive in the preparation of a spreadable 5-ASA medicament for the topical treatment of oral ulcerations, inflammation, or lesions of the oral cavity.
2. Use of 5-ASA or a physiologically acceptable derivative thereof as an active in a glyceryl monooleate containing topical medicament for the treatment of oral ulcerations, inflammation, or lesions of the oral cavity.
3. The use of 5-ASA or a physiologically acceptable derivative thereof and glyceryl monooleate in the preparation of a spreadable medicament for the topical treatment of oral ulcerations, inflammation, or lesions of the oral cavity.
4. A method of treating oral ulcerations, inflammation, or lesions of the oral cavity comprising spreading topically over the ulcer lesion, or inflamed mucosa, a pharmaceutical formulation comprising an effective amount of 5-ASA or a physiologically acceptable derivative thereof, and glyceryl monooleate.
5. Since we have also discovered that 5-ASA can particularly treat oral aphthous ulcers, oral mucositis, oral Crohn's disease and orofacial granulomatosis, a yet further aspect of the invention relates to the use of 5-ASA (in any composition) for the treatment of these oral disorders.

The invention will now be described by way of example with reference to the following compositions.

EXAMPLE 1

|  | % w/w |
|---|---|
| Active Constituent | 5.0 |
| 5-Aminosalicylic acid | |
| Other Constituents | |
| Myverol ™ 18-99 | 53.5 |
| (Monoglyceride) | |
| White Soft Paraffin | 35.0 |
| Titanium Dioxide | 5.0 |
| Benzyl Alcohol | 1.0 |
| Ascorbyl Palmitate | 0.5 |
| Total: | 100.0 |

EXAMPLE 2

Example 1 was repeated, but without the addition of benzyl alcohol, and compensated for by increasing the weight of white soft paraffin.

EXAMPLE 3

Example 1 was substantially repeated but lidocaine hydrochloride was additionally added as a local anaesthetic and benzyl alcohol taken out. The % w/w Myverol™ was decreased by a few units.

EXAMPLE 4

Oral mucositis following chemotherapy is a common problem. 15 patients suffering from oral mucositis were asked to apply a 5-ASA/myverol composition prepared in accordance with Example 1. All patients used chlorohexidine mouthwash and may have received benzydamine hydrochloride mouthwash and opioid analgesics. Each patient was asked to fill in a questionnaire at the end of a fifteen month study period. Of the 14 replies received, 2 patients were unable to recall details. Of the remaining 12 patients, 10 derived "overall" pain relief, 9 deriving relief on eating, 7 on drinking, and only 2 reported discomfort on application.

This study suggests that topical 5-ASA, particularly in a topical glyceryl monooleate composition, is of benefit in the management of chemoradiotherapy induced mucositis.

EXAMPLE 5

A 14 year old boy with Crohn's Disease was asked to apply the composition in accordance with Example 1 twice daily for six weeks. The oral Crohn's Disease produced a thickening of the mucous membranes in the mouth and lip and in this patient was associated with perianal disease. During the treatment there was also a clear improvement inside the mouth, but very little difference to the lips.

EXAMPLE 6

A 12 year old boy with Melkerson-Rosenthal syndrome or orofacial granulomatosis had biopsies taken from his mouth which did not show granulomas diagnostic of Crohn's Disease. Otherwise the patient had symptoms identical to oral Crohn's Disease, but there was no evidence of a gut problem.

The patient's symptoms included thickening of the lower lip and buccal mucosa, furrowing of the tongue and recurrent apthous ulceration. After one month applying a composition in accordance with the examples, the patient was very pleased with his progress. Remarkably he developed only two ulcers during the treatment period.

What is claimed is:

1. A substantially water-free spreadable mucoadhesive pharmaceutical composition for topical administration to a treatment location in the oral cavity, said composition comprising about 3% to about 7% w/w of a 5-aminosalicylic acid compound selected from 5-aminosalicylic acid and physiologically acceptable derivatives thereof, about 40% to about 60% w/w glyceryl monooleate, and about 25% to about 45% w/w white soft paraffin and being spreadable to form an adhesive film over the treatment location to maintain the 5-aminosalicylic acid compound in contact with the treatment location.

2. A method of treating oral ulcerations, inflammation, or lesions of the oral cavity comprising forming a film containing an effective amount of a 5-aminosalicylic acid compound selected from 5-aminosalicylic acid and physiologically acceptable derivatives thereof by spreading topically over the ulcer, lesion or inflamed mucosa, a substantially water-free pharmaceutical formulation comprising about 3% to about 7% w/w of the 5-aminosalicylic acid compound, about 40% to about 60% w/w glyceryl monooleate and about 25% to about 45% w/w white soft paraffin.

3. The method as claimed in claim 2 wherein the pharmaceutical formulation comprises about 5% w/w 5-aminosalicylic acid, about 50% w/w glyceryl monooleate, and about 35% w/w white soft paraffin.

4. The composition as claimed in claim 1 comprising at least one of 1% to 5% w/w anesthetic agent and 0.1% to 1% w/w antioxidant.

5. The composition as claimed in claim 4 wherein the anaesthetic agent is a lidocaine anaesthetic agent and the antioxidant is ascorbic palmitate.

6. The composition as claimed in claim 1 wherein glyceryl monooleate is present as monoolein.

7. The composition as claimed in claim 1 comprising about 5% w/w 5-aminosalicylic acid, about 50% w/w glyceryl monooleate, and about 35% w/w white soft paraffin.

8. The composition as claimed in claim 1 further comprising at least one component selected from anaesthetic agents, flavorings, surfactants, penetration enhancers, antioxidants, polymers, and opacifiers.

9. The composition as claimed in claim 8 comprising at least one of 1% to 5% w/w anaesthetic agent and 0.1% to 1% w/w antioxidant.

* * * * *